(12) United States Patent
Dayton (10) Patent No.: US 9,095,633 B1
(45) Date of Patent: Aug. 4, 2015

(54) OBJECT DECONTAMINATION APPARATUS WITH AN ADJUSTABLE ULTRAVIOLET SOURCE

(71) Applicant: Daylight Medical, Inc., Middleburg Heights, OH (US)

(72) Inventor: Roderick M. Dayton, Strongsville, OH (US)

(73) Assignee: DAYLIGHT MEDICAL, Middleburg Heights, OH (US)

( * ) Notice: Subject to any disclaimer, the term of this patent is extended or adjusted under 35 U.S.C. 154(b) by 0 days.

(21) Appl. No.: 14/530,510

(22) Filed: Oct. 31, 2014

Related U.S. Application Data (60) Provisional application No. 62/072,577, filed on Oct. 30, 2014.

(51) Int. Cl.
*A61L 2/10* (2006.01)

(52) U.S. Cl.
CPC ............... *A61L 2/10* (2013.01); *A61L 2202/14* (2013.01); *A61L 2202/16* (2013.01); *A61L 2202/25* (2013.01)

(58) Field of Classification Search
CPC ....... G21F 9/00; G21F 9/001; A61K 41/0009; A61L 2/00; A61L 2/08; A61L 2/10; A61L 2/0029; A61L 2/0047; A61L 2202/14; A61L 2202/16; A61L 2202/25
See application file for complete search history.

(56) References Cited

U.S. PATENT DOCUMENTS

| | | | |
|---|---|---|---|
| 5,039,867 A | 8/1991 | Nishihara | |
| 6,861,658 B2 | 3/2005 | Fiset | |
| 7,198,624 B2 | 4/2007 | Muzzi | |
| 7,229,467 B2 | 6/2007 | Spivak | |
| 7,476,885 B2 | 1/2009 | Garcia | |
| 7,476,888 B2 | 1/2009 | Fiset | |
| 7,626,187 B2 | 12/2009 | Younts | |
| 7,721,383 B2 | 5/2010 | Garcia | |
| 7,819,910 B2 | 10/2010 | Fiset | |
| 7,921,853 B2 | 4/2011 | Fiset | |
| 7,923,707 B2 | 4/2011 | Garcia | |
| 7,994,489 B2 | 8/2011 | Fiset | |
| 8,067,750 B2 | 11/2011 | Deal | |
| 8,105,532 B2 | 1/2012 | Harmon | |
| 8,186,004 B2 | 5/2012 | Garcia | |
| 8,226,887 B2 | 7/2012 | Harmon | |
| 8,330,121 B2 | 12/2012 | Douglas | |
| 8,455,832 B2 | 6/2013 | Statham | |
| 8,662,705 B2 | 3/2014 | Roberts | |
| 8,680,496 B2 | 3/2014 | Leben | |
| 8,682,576 B2 | 3/2014 | Kurtti | |
| 8,791,441 B1 | 7/2014 | Lichtblau | |
| 8,816,301 B2 | 8/2014 | Stibich | |
| 8,841,634 B2 | 9/2014 | Statham | |
| 8,859,994 B2 | 10/2014 | Deal | |
| 2003/0216795 A1 | 11/2003 | Harth | |

(Continued)

*Primary Examiner* — Francis M Legasse, Jr.
(74) *Attorney, Agent, or Firm* — Pearne & Gordon LLP (57) ABSTRACT

Provided is a decontamination apparatus including a base, and a source that emits UVC light at a suitable intensity to at least partially decontaminate a target object and render the target object pathogen reduced. An adjustable support is coupled to the base and includes an adjustment mechanism that can be manipulated to adjust a position of the source relative to the base. A controller is operatively connected to the source to control emission of the UVC light and establish at least one of a suitable duration of a decontamination process and a suitable intensity of UVC light to render the target object pathogen reduced.

22 Claims, 9 Drawing Sheets

(56) References Cited

U.S. PATENT DOCUMENTS

| | | |
|---|---|---|
| 2004/0175290 A1 | 9/2004 | Scheir |
| 2004/0249369 A1* | 12/2004 | Muzzi et al. ............ 606/9 |
| 2009/0143842 A1 | 6/2009 | Cumbie |
| 2010/0032589 A1 | 2/2010 | Leben |
| 2010/0104471 A1* | 4/2010 | Harmon et al. ............ 422/24 |
| 2011/0243789 A1* | 10/2011 | Roberts ............ 422/24 |
| 2011/0256019 A1* | 10/2011 | Gruen et al. ............ 422/24 |
| 2012/0093688 A1 | 4/2012 | Harmon |
| 2012/0243789 A1 | 9/2012 | Yang |
| 2012/0282135 A1 | 11/2012 | Trapani |
| 2013/0002445 A1 | 1/2013 | Stibich |
| 2013/0234041 A1 | 9/2013 | Deal |
| 2013/0243647 A1 | 9/2013 | Garner |
| 2013/0280126 A1 | 10/2013 | Statham |
| 2014/0044590 A1 | 2/2014 | Trapani |
| 2014/0212332 A1 | 7/2014 | Bergman |
| 2014/0227132 A1 | 8/2014 | Neister |

\* cited by examiner

OBJECT DECONTAMINATION APPARATUS WITH AN ADJUSTABLE ULTRAVIOLET SOURCE

CROSS-REFERENCE TO RELATED APPLICATIONS

This application claims the benefit of U.S. Provisional Application No. 62/072,577, filed Oct. 30, 2014, which is incorporated in its entirety herein by reference.

BACKGROUND OF THE INVENTION

1. Field of the Invention

This application relates generally to a decontamination method and apparatus and, more specifically, to an apparatus and method for emitting ultraviolet light onto surfaces of a room for decontamination purposes.

2. Description of Related Art

Surfaces in rooms at healthcare facilities are commonly exposed to infectious organisms and other biologically-active contaminants (hereinafter generally referred to as "contaminants") spread by the patients who occupy those rooms. These contaminants can remain viable on the contaminated surfaces to reproduce and infect others such as subsequent patients and/or visitors, for example, who enter the room and make contact with those surfaces. In an effort to prevent the spread of infections, healthcare facilities must conduct decontamination procedures in the rooms as frequently as possible.

One example of a room where such contaminants are prevalent is an inpatient hospital room. Surfaces such as tray tables, bed rails, and television remote controls frequently come into direct contact with patients during their stay in the room. These surfaces should be decontaminated frequently to avoid a buildup of contaminants and minimize the risk of spreading an infection from the patient to another person who may come into contact with the surfaces. However, manually decontaminating such rooms is labor intensive, requiring personnel to adhere to strict guidelines governing the use of liquid disinfectants. Further, depending on the surfaces being decontaminated, it may not be practical to provide the entirety of the surfaces with liquid disinfectants in compliance with those guidelines.

BRIEF SUMMARY OF THE INVENTION

According to one aspect, the subject application involves a decontamination apparatus including a base, and a source that emits UVC light at a suitable intensity to at least partially decontaminate a target object and render the target object pathogen reduced. An adjustable support is coupled to the base and supports the source, the adjustable support including an adjustment mechanism that is manipulable to adjust a position of the source relative to the base. A range sensor senses a property indicative of a distance separating the source of UVC light from the target object to be rendered pathogen reduced. A controller is operatively connected to the source to control emission of the UVC light. The controller is in communication with the range sensor to receive a signal indicative of the distance separating the source from the target object as sensed by the range sensor and includes a variable component that establishes at least one of a duration of a decontamination process and the suitable intensity of UVC light as a function of the distance separating the source from the target object.

According to another aspect, the subject application involves a decontamination apparatus that includes a base, and a first arm adjustably coupled to the base to allow an orientation of the first arm to be adjusted relative to the base. The first arm includes a longitudinally-adjustable segment that allows a length of the arm to be adjusted. A first source is coupled adjacent to a distal end of the first arm, emits UVC light at a suitable intensity to at least partially decontaminate a first target object and render the first target object pathogen reduced. A controller is operatively connected to the first source to control emission of the UVC light onto the first target object.

According to yet another aspect, the subject application involves a decontamination apparatus that includes a base, and a source that emits UVC light at a suitable intensity to at least partially decontaminate a target object and thereby render the target object pathogen reduced. The source includes a UVC bulb that is operable to emit the UVC light, and a reflective shield arranged adjacent to the UVC bulb to reflect at least a portion of the UVC light emitted by the UVC bulb generally away from the target object in a focused direction, generally toward the target object. The reflective shield includes a plurality of arcuate regions, each extending about a different axis with a different orientation. An adjustable support is coupled to the base and supports the source. The adjustable support includes an adjustment mechanism that can be manipulated to adjust a position of the source relative to the base. A controller is operatively connected to the source to control emission of the UVC light by the source.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

Figure 1:
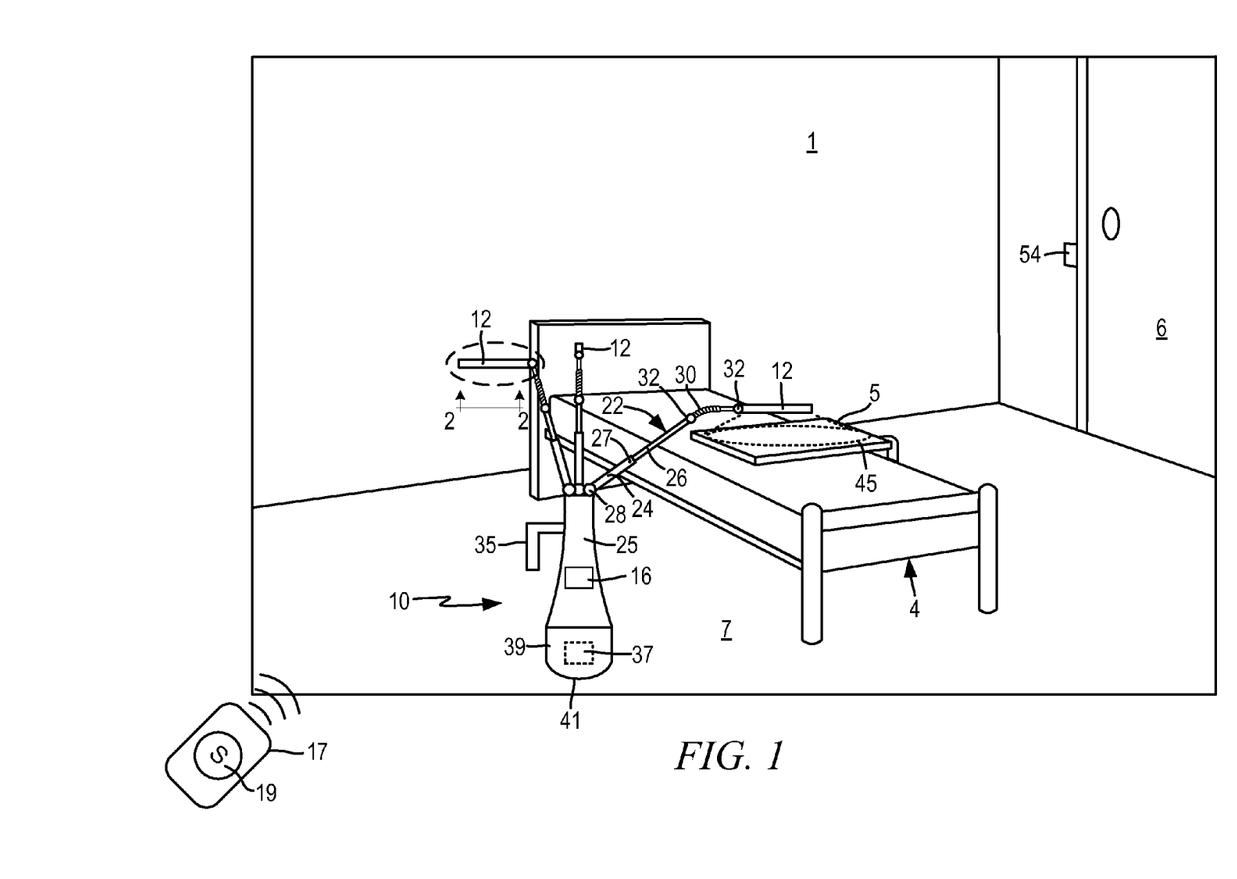
FIG. 1 shows a schematic representation of a decontamination system installed in an inpatient hospital room.

FIG. 1 shows an illustrative embodiment of an inpatient room 1 in a hospital that is accessible through a door 6 separating the inpatient room from a hallway, for example. The room 1 is provided with a patient bed 4 and a tray table 5 that can extend over the patient lying in the bed 4. Although not shown, the room 1 can also include other fixtures and features commonly found in inpatient rooms such as a television, health-monitoring equipment such as a heart-rate monitor, telephone, nightstand, etc. . . . . Further, although the present disclosure focuses on the decontamination of items within an inpatient hospital room 1 for the sake of clarity and brevity, the technology disclosed herein can be used to decontaminate objects located anywhere, such as in hotel rooms any other public accommodations.

Also disposed within the room 1 shown in FIG. 1 is a decontamination apparatus 10 operable to at least partially decontaminate, or at least render pathogen reduced, contaminated surfaces such as the tray table 5 within that room 1. The decontamination process can be initiated manually, and performed by the decontamination apparatus 10 on demand, and/or can optionally be initiated automatically according to a predetermined schedule when the room 1 is unoccupied, as determined utilizing a plurality of sensors as described below.

Rendering the surfaces "pathogen reduced" with the decontamination apparatus 10 does not necessarily require the subject surfaces to be 100% sterile, free of any and all living organisms that can viably reproduce. Instead, to be considered pathogen reduced, there must be a lower level of living contagions on the decontaminated surfaces capable of reproducing or otherwise causing an infection after performance of the decontamination process than the level that existed on the surfaces prior to performance of the decontamination process. For example, the exposed surfaces in the bathroom can be considered to be pathogen reduced if at least a 1 $\log_{10}$ reduction of such contagions on the surfaces remain infectious (i.e., no more than 1/10th of the biologically-active contagions originally on the exposed surfaces remain active or infectious at a time when the decontamination process is completed) occurs. According to yet other embodiments, the surfaces can be considered pathogen reduced once at least a 3 $\log_{10}$ reduction (i.e., 1/1,000th) of such contagions on the surfaces is achieved.

Generally, the decontamination apparatus 10 includes one or a plurality of sources 12 that direct a disinfecting agent toward the surface(s) to be rendered pathogen reduced, a redundant occupant sensing system that determines whether the room 1 is occupied or not, and a controller 16 that interferes with emission of the disinfecting agent by the source(s) 12 if the room 1 is, or becomes occupied based on a signal from the occupant sensing system. Each source 12 can be any apparatus that emits a disinfecting agent that, when exposed to the surfaces to render those exposed surfaces pathogen reduced. For the illustrative embodiments described herein and shown in the drawings, each source 12 is an ultraviolet source that is to be energized to emit UVC light as the disinfecting agent, and the surface to be rendered pathogen reduced is the tray table 5.

As shown, each source 12 includes at least one, and optionally a plurality of UVC bulbs 14 (FIG. 2) coupled to a reflective shield 18 coupled to an underside of a housing 20. The housing 20 can be pivotally coupled to a distal end of an articulated arm 22 or other suitable support that allows the housing 20, and accordingly the bulbs 14, to be pivoted about a rotational axis in the directions indicated by arrow 21 and otherwise positioned in a suitable position relative to the tray table 5 to achieve the desired level of decontamination within a predetermined period of time, once activated.

According to the embodiment in FIG. 1, each arm 22 has a portion including an adjustable length extending generally away from a base portion 25, which can be facilitated by an external member 24 that telescopically receives an internal member 26, or other suitable length adjustment mechanism (e.g, sliding track, etc. . . . ). A locking member 27 such as a spring-biased pin urged toward a locking position, etc. . . . can be provided to one or both of the external and internal members 24, 26 to maintain a desired length of the arm 22, once manually established. A hinge 28 or other connector suitable to allow angular adjustment of the arm 22 relative to the base 25 can be disposed between the base 25 and the arm 22. A bendable joint 30 can also be provided anywhere along the length of the arm 22, such as adjacent to the distal end of the arm 22 where the housing 20 is supported. The joint 30 can be formed from a plastically-deformable flexible material that can be manually bent to position the housing 20, yet be sufficiently rigid to maintain the position of the housing relative to the arm 22 once the bending force has been removed. Further, a hinge 32 can also optionally be positioned along the arm 22 before and/or after the joint 30 to allow further adjustment of the position of the housing 20 and bulbs to achieve the desired coverage of the tray table 5 with UVC light. As with any of the hinges described herein, the hinge(s) 32 can be selectively lockable, meaning a locking member such as a set screw, for example, can be loosened to allow the structures coupled to opposite sides of the hinge(s) 32 to be pivotally adjusted relative to each other. Once the desired adjustment has been completed, the set screw or other locking member can be tightened to interfere with further pivotal adjustment of the structures relative to each other.

The base 25 supports the arms 22 at a desired elevation above the floor 7 of the room 1. The base 25 supports the controller 16 that can be manipulated by a user to control operation of the decontamination apparatus 10 (e.g., independently control operation of each source 12 to emit UVC light, optionally to cause one source 12 to remain energized longer than another one of the sources 12), and optionally houses an on-board power supply such as a rechargeable battery bank 37 storing electric energy that can be used to energize the bulbs 14 and power the controller 16. Being relatively heavy, the battery bank 37 can be housed within a recess defined by a lower cap 39 of the base 25 comprising an arcuate bottom surface 41 that rests on the floor 7. The arcuate bottom surface 41 allows the decontamination apparatus to wobble, if necessary, to properly position the bulbs 14 for a decontamination process. The base 25, or another portion for the decontamination apparatus can optionally be provided with an accelerometer, tip sensor, gyroscope or other type of monitoring device that can sense when the decontamination apparatus 10 has been picked up, falls over, moved or otherwise disturbed. In such events, an active decontamination process can be terminated and a new decontamination process can be prevented from being initiated. The lower cap 39 can be threadedly connected to the base 25 so as to be removable, and optionally interchangeable. For removable embodiments, the lower cap 39 can be unscrewed from the base 25 to grant access to the battery bank 37. A depleted battery bank 37 can then be removed from the decontamination apparatus 10 and replaced with a charged battery bank 37. For embodiments where the battery bank 37 is integrated into the lower cap 39, the lower cap with the depleted battery bank 37 can be replaced in its entirety with another lower cap 39 with a charged battery bank 37. According to alternate embodiments, the decontamination apparatus can include a power cord that is to be plugged into an AC mains electric outlet supplied by an electric power utility to obtain the electric energy needed to power the decontamination apparatus 10.

The base 25 can also optionally be provided with a connector, shown in FIG. 1 as a hook 35 that is generally shaped to resemble an upside-down "L". The hook 35 can be placed over a receiver or other portion of a cart hauling cleaning supplies, for example, or any other transport vehicle, to allow transportation of the decontamination apparatus 10 throughout the hospital for use in a plurality of different rooms 1.

The embodiments of the base 25 are described above as a static structure that supports the arms 22 at a desired elevation above the floor 7 of the room 1 and optionally housing a battery bank 37. However, alternate embodiments of the base 25' are schematically shown in FIGS. 5-8. The base 25', according to such alternate embodiments, includes a plurality (e.g., three in the illustrated embodiment) of arcuate panels 82, each pivotally coupled by a hinge 84 or other adjustable fastener to static portion 86 of the base 25' to which the arms 22 are coupled. Each panel 82 has an arcuate shape across a lateral dimension, to form approximately one third (⅓) of the total circumference of the substantially-tubular base 25' when adjusted to the stowed configuration. In the stowed configuration, each panel 82 extends substantially vertically upward from the static portion 86 of the base 25' to define an internal chamber 88 into which the arms 22, and optionally the bulbs 14, are at least partially recessed while the decontamination apparatus 10 is in the stowed configuration. Inward-facing surfaces of each panel 82 can optionally be coated with, or otherwise formed from a light-colored material (e.g., white, off white, cream, light gray, etc. . . . ) and/or a reflective material (e.g., metallic, reflective plastic, etc. . . . ) to enhance the reflectivity of UVC light emitted by the bulbs 14 while at least partially recessed in the chamber 88. Thus, in the stowed configuration after being used to decontaminate a surface in a hospital room, for example, where the inward-facing surfaces of the panels 82 could be exposed to a biologically-active pathogen, the bulbs 14 can be activated to emit UVC light. This UVC light will be reflected by the inward-facing surfaces of the panels 82, thereby promoting complete exposure of the entire internal periphery of the chamber 88. Such activation of the bulbs 14 can decontaminate the inward-facing surfaces of the panels 82, thereby mitigate the risk of spreading the pathogen from one environment to another as the decontamination apparatus 10 is transported there between.

Figure 7:
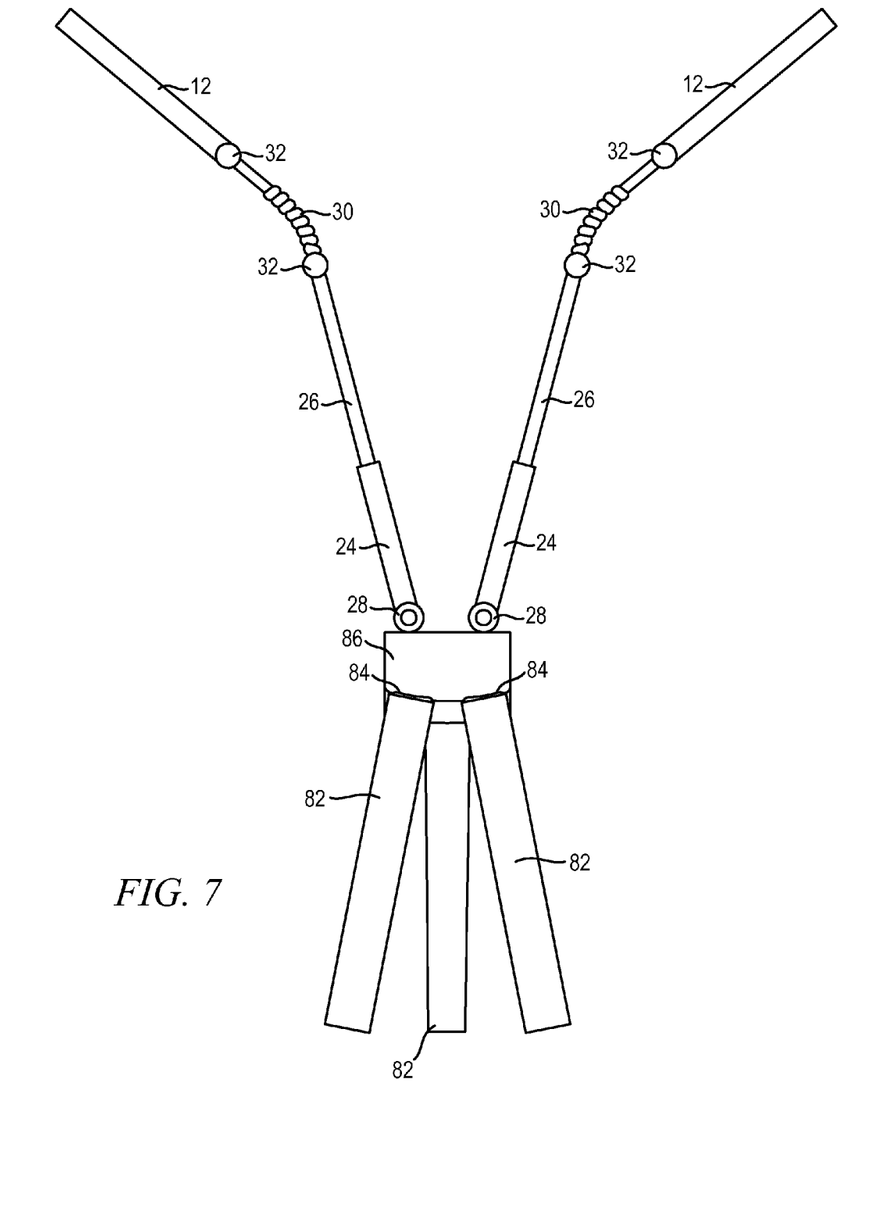
FIG. 7 shows the alternate embodiment of the decontamination apparatus appearing in FIG. 5 with the base in a deployed configuration in which the decontamination apparatus is to be used to decontaminate a surface.
Figure 8:
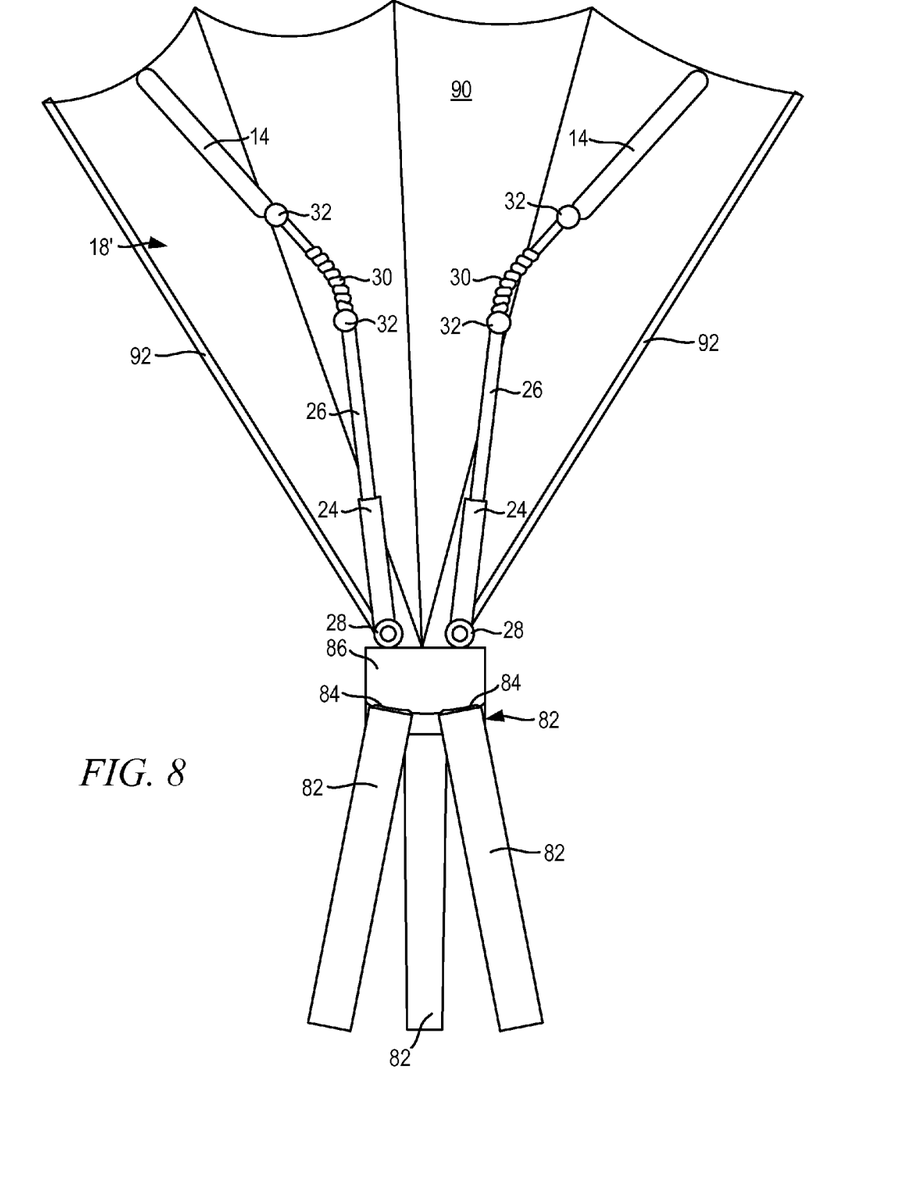
FIG. 8 shows the alternate embodiment of the decontamination apparatus appearing in FIG. 6 with the base in a deployed configuration in which the decontamination apparatus is to be used to decontaminate a surface.

The base 25' can be converted from the stowed configuration to a deployed configuration, shown in FIGS. 7 and 8, in which the decontamination apparatus 10 is ready for use. Such a conversion can be achieved by pivotally adjusting the panels 82 about their respective hinges 84, such that the panels 82 extend downward from the static portion 86 at an angle (e.g., between about 45° and 90° from horizontal). The inward-facing surfaces of the panels 82 are adjusted to become substantially outward-facing surfaces in the deployed configuration, thereby exposing those surfaces to the elements within the room in which the decontamination apparatus 10 is located. In the deployed configuration, the panels 82 act as legs that separate the static portion 86 from an underlying ground surface, and elevate the static portion 86 and arms 22 to a height above the underlying ground surface suitable for performing the desired decontamination process.

Figure 2:
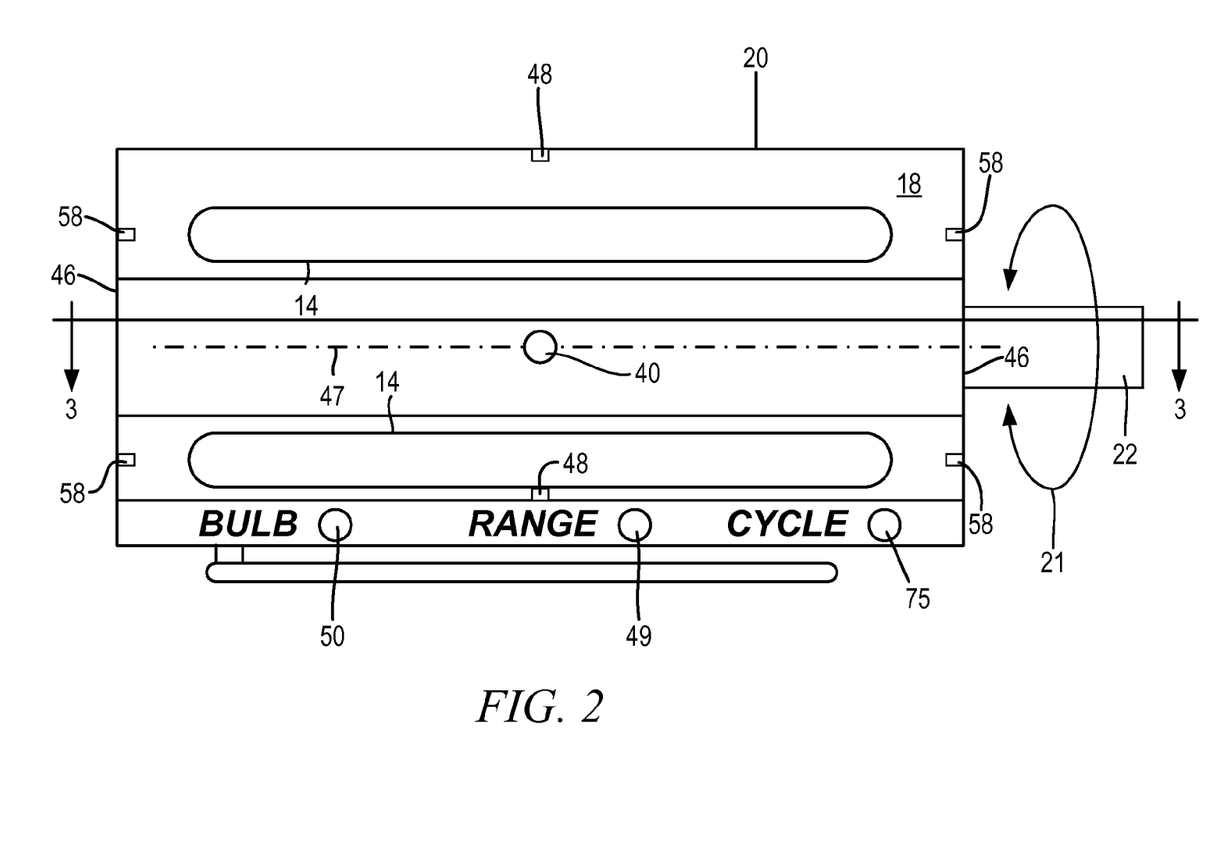
FIG. 2 is a bottom view of a source of a disinfecting agent in the form of UVC light, the source being provided adjacent to a terminal end of an articulated arm and being viewed from the perspective indicated by line 2-2 in FIG. 1.
Figure 9:
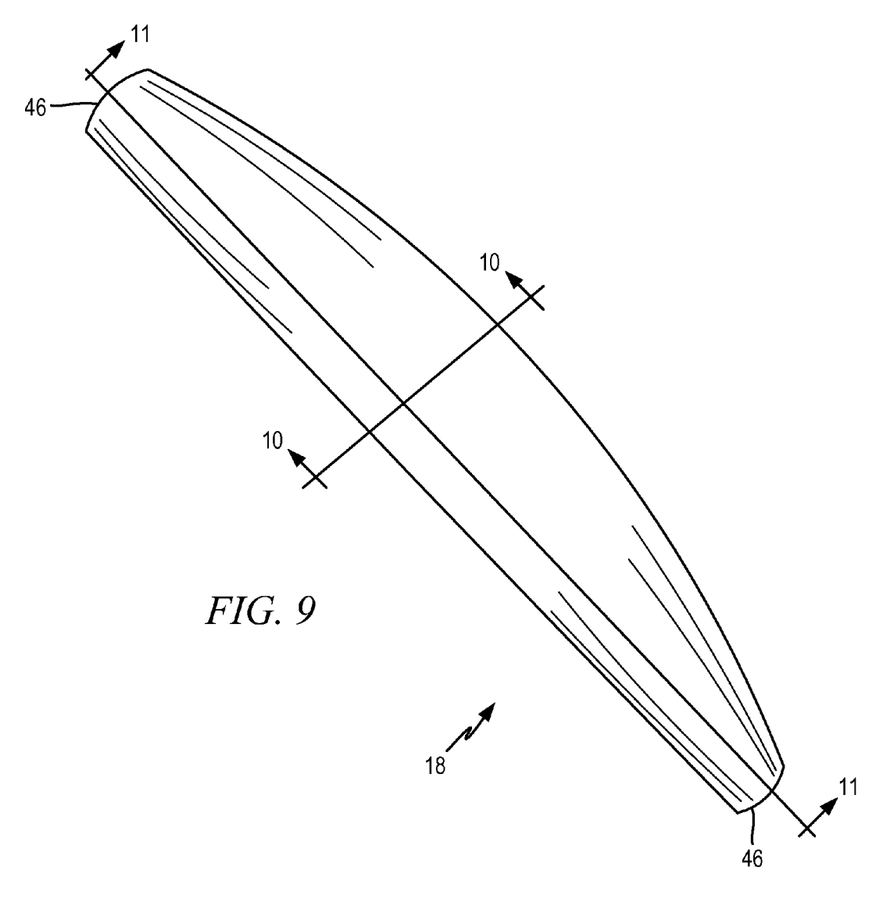
FIG. 9 shows a perspective view of a reflective shield for directing UVC light toward a target surface.
Figure 10:
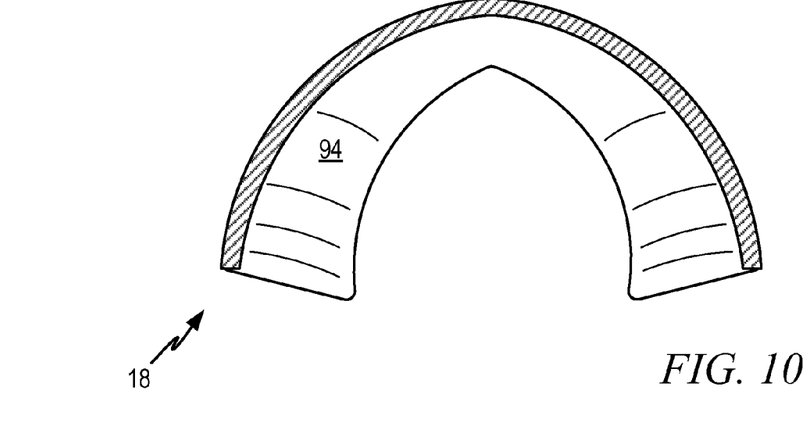
FIG. 10 is a sectional view of the reflective shield shown in FIG. 9 taken along line 10-10.
Figure 11:
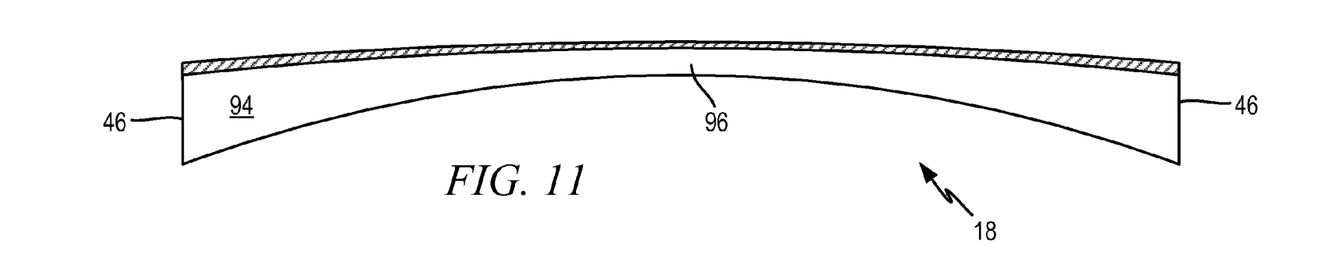
FIG. 11 is a sectional view of the reflective shield shown in FIG. 9 taken along line 11-11.

The reflective shield 18 in FIG. 2 includes an arcuate or paneled region 34 that is configured to reflect UVC light emitted upwardly from the bulbs 14 in a downward direction, generally towards the tray table 5 where the UVC light can decontaminate the exposed surfaces thereof. The arcuate or paneled region 34 can include a continuous curvature in multiple planes or a plurality planar and reflective structures arranged to form a somewhat curved profile to achieve the desired light pattern for the tray table 5 or other object being decontaminated. For example, and as schematically illustrated in FIGS. 9-11, the reflective shield 18 can include a reflective surface 94 that faces the bulbs 14 that has a gradually varying, or at least a variable, radius of curvature in a transverse direction relative to a longitudinal axis 47 along the length of that longitudinal axis 47 (FIG. 2). For example, the radius of curvature of the reflective surface of the reflective shield 18 can be greatest at a central region 96 (FIG. 11) adjacent to the location of a focal indicator 40, described below. The radius of curvature in the transverse direction is less than the radius of curvature at this central region at locations further toward opposite, longitudinal ends 46 of the reflective shield 18 along the longitudinal axis 47. The radius of curvature can optionally be the smallest at those longitudinal ends 46. Although the radius of curvature is used to describe the shape of the reflective surface of the reflective shield 18, it is to be understood that the cross-sectional shape of the reflective surface does not necessarily have a constant radius of curvature. In other words, the cross sectional shape of the reflective surface 94 taken along line 10-10 in FIG. 9, a cross section that is depicted in FIG. 10, can be a downward-opening parabolic shape, or other desired arcuate shape that more-narrowly focuses UVC light emitted by the bulbs 14 in the transverse direction adjacent to the longitudinal ends 46 than adjacent to the central region along the longitudinal axis 47.

To help with adjustment of the housing 20 and/or reflective shield 18, a focal indicator 40 can optionally be provided to the reflective shield 18 and/or housing 20. Locating the focal indicator 40 between the UVC bulbs 14 as shown in FIG. 2 allows the focal indicator to identify a general direction that is representative of the direction in which the UVC light from the UVC bulbs 14 will be focused. The focal indicator 40 can include a light emitting diode ("LED"), laser light, or other optical indicator that can project light that will illuminate a region of a surface on which the UVC light from the UVC bulbs 14 is centered. An example of such a region is illustrated in FIG. 1 by the broken lines 45 appearing on the tray table 5. Thus, a user can essentially aim the UVC light toward the surfaces to be rendered pathogen reduced, and get a sense of the portion of the tray table 5 that will be suitably exposed to the UVC light during a decontamination apparatus to be considered pathogen reduced within a predetermined period of time for the power of the bulbs 14 employed.

Figure 6:
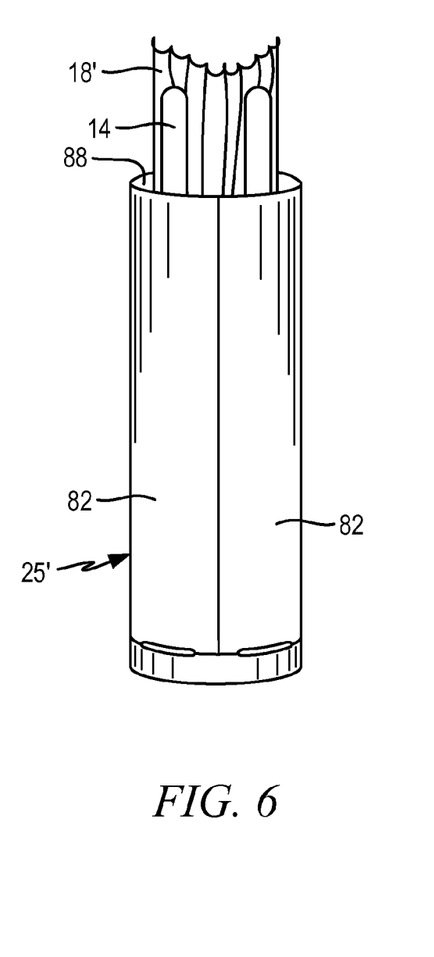
FIG. 6 shows a side view of an alternate embodiment of a decontamination apparatus including a base in a stowed configuration for transportation of the decontamination apparatus.

FIG. 8 shows an alternate embodiment of the reflective shield 18'. Unlike the embodiments described above involving a separate reflective shield 18 provided to each source 12, the present embodiment includes a collapsible shield 18' that is configured to reflect UVC light emitted by a plurality (e.g., two illustrated in FIG. 8) of bulbs 14. As shown, the reflective collapsible shield 18' includes an aluminized or otherwise metalized Mylar (e.g., stretched polyester film, also commonly referred to as biaxially-oriented polyethylene terephthalate or "BoPET", for short) sheet 90 spanning a distance between poles 92 extending in different, optionally diverging or opposite directions from the static portion 86 of the base 25'. Mylar is one example of a suitable reflective surface that is collapsible, but the present disclosure is not so limited, as any reflective surface that can be collapsed to fit within the chamber 88 of the base 25' in the stowed configuration will suffice. One or each of the poles 92 can optionally be spring biased, urged by gravity or otherwise urged toward their diverging orientations in which the sheet 90 is pulled substantially taut to form a reflective surface extending between the poles 92. To convert the decontamination apparatus 10 to its stowed configuration, the poles 92 are adjusted toward each other, allowing the sheet 90 to be folded in a fan-like manner to fit within the chamber 88 formed by the panels 82 of the base 25', as shown in FIG. 6.

The embodiment of the source 12 shown in FIG. 2 includes a plurality of elongated UVC bulbs 14 that emit UVC light as the disinfecting agent. Since such a source 12 emits only UVC light, it is dedicated for performing the decontamination process described herein. But regardless of the configuration of the UVC bulbs 14, the source 12 can optionally include an intensity sensor 48 that senses an intensity of the UVC light emitted by each UVC bulb 14 present. For the sake of brevity, the present technology will be described hereinafter with reference to the elongated UVC bulbs 14, although any other desired configuration of UVC bulb is a viable alternative. The intensity of the UVC light emitted by the UVC bulbs 14 will diminish over time. To promote thorough decontamination of the exposed surfaces in the room 1 with a reasonable cycle time for the decontamination process, the intensity sensors 48 include a photosensitive component such as a photodiode, charge coupled device, etc. . . . , operatively coupled to the controller 16 to monitor the intensity of the UVC light from the UVC bulbs 14. A signal indicative of the sensed intensity is transmitted to the controller 16, which is operatively connected to at least receive signals transmitted by the intensity sensor 48 and the sensors of the redundant occupant sensing system as described below. Based at least in part on the signal from the intensity sensor 48, the controller 16 can issue a notification that one or more of the UVC bulbs 14 is nearing the end of its useful life, and should be replaced. Such a notification can include the illumination of a visible indicator in the form of a LED 50 provided to the source 12 itself, or to an appropriate LED 52 (FIG. 4) provided to the controller 16, which can optionally be remotely located from the source 12 but in communication with the source 12 via a communication channel such as a hardwired or wireless connection, or optionally integrated as part of the source 12 itself. According to alternate embodiments, the controller 16 can optionally be in wireless communication with a portable fob 17 (FIG. 1) having limited control features. For the illustrated embodiment appearing in FIG. 1, for example, the portable fob 17 allows an operator to issue a START command by selecting a start button 19 to commence a decontamination cycle from a location that is remote (e.g., externally of the room in which the decontamination apparatus 10 is located) from the decontamination apparatus 10. The portable fob 17 and/or the controller 16 can optionally be configured to commence decontamination cycles of varying durations based, at least in part, on the number of times the start button 19 is selected. Although the illustrated embodiment of the portable fob 17 in FIG. 1 includes a start button 19, it can optionally lack a stop button or any other feature that would allow the operator to terminate the decontamination cycle, on demand, from the remote location.

Figure 3:
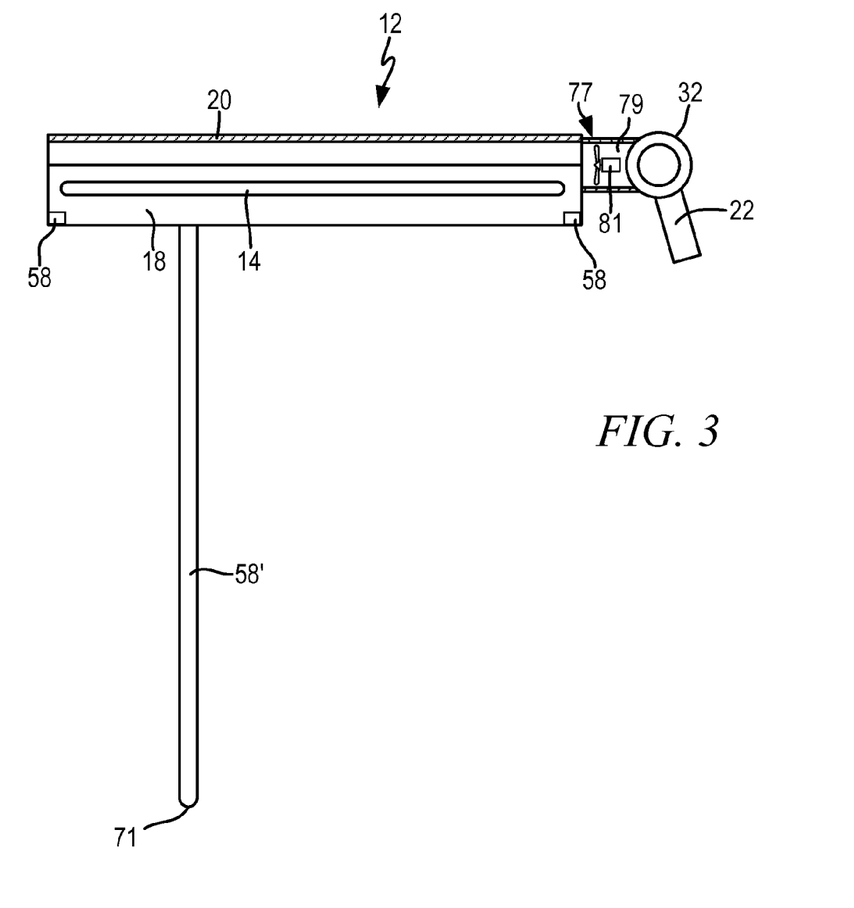
FIG. 3 is a partially-cutaway side view of the source taken along line 3-3 in FIG. 2.

FIG. 3 shows a partially-cutaway side view of the source 12 taken along line 3-3 in FIG. 2. To promote the longevity of the UVC bulbs 14 provided to the source 12, a coupling 77 is arranged between the housing 20 and the hinge 32. The coupling 77 defines an interior passage 79 in which an electric fan 81 is located. The Electric fan 81 can be powered with electric energy supplied by the battery bank 37, with electric energy supplied from the AC mains wall outlet, etc. . . . to direct cooling air over the UVC bulbs 14.

Further, one or a plurality of proximity sensors 58, interchangeably referred to as range sensors 58, can be arranged, optionally as an array, to sense a proximity of the housing, which is indicative of the proximity of the bulbs 14, to the tray table 5 or other object to be rendered pathogen reduced. For example, the proximity sensors 58 can sense light from a light source that is reflected from the tray table 5 to determine the approximate spacing of the housing and 20 and/or bulbs 14 from the tray table 5. Other embodiments of the proximity sensors 59 can utilize a sensed capacitance value to determine such a proximity. According to yet other embodiments, an ultrasonic range finder includes an ultrasonic transceiver that emits high-frequency sound waves (e.g., frequencies, such as those above 20 kHz, or otherwise above the upper limit of the human audio spectrum) and evaluates the echo which is received back by the sensor 58, measuring the time interval between sending the signal and receiving the echo to determine the distance to the object to be rendered pathogen reduced. Regardless of the technology utilized, arranging the proximity sensors 58 in an array or at least positioning one proximity sensor 58 at a known location promotes proper positioning of the bulbs 14 relative to the surface of the tray table 5 to achieve the desired level of decontamination utilizing a decontamination process with a predetermined duration. In other words, a scenario where one end of each bulb 14 is relatively close to the surface of the tray table 5 and the other, opposite end of each bulb 14 is relatively far from the surface of the tray table can be avoided through use of the proximity sensors 58. If a significant departure from the uniform spacing of the bulbs 14 from the tray table 5 is detected, a warning can be audibly broadcast from a speaker 61 provided to the controller 16, presented as the illumination of a LED on the controller and/or the offending source 12, etc. . . . to help the operator correctly orient the source 12.

According to other embodiments, the proximity sensors 58 can be utilized to ensure the source 12 is positioned close enough to the tray table 5 to achieve the desired level of decontamination during performance of the decontamination process. The controller 16 can optionally be configured to automatically (e.g., without human intervention directed specifically toward specifying the length of the decontamination process) adjust the duration of the decontamination process based, at least in part, on the distance separating the source 12 from the tray table 5. For example, the one or more proximity sensors 58 senses a distance separating the tray table 5 from the source 12, and transmits a signal indicative of this distance to the controller 16. Based on this signal, the controller 16 can determine the approximate value of the separation, and determine a length of the decontamination process such that the desired level of decontamination is achieved once the decontamination with the adjusted length is completed. As a specific example, based on the signal from the proximity sensor(s) 58, the controller 16 can determine whether the source 12, or at least the bulbs 14 are within eighteen (18 in.) inches of the tray table 5. If so, a range indicator 49 such as the LED shown in FIG. 2 provided to the source 12 can be illuminated green to indicate that the source 12 is sufficiently close to the tray table 5 for a sixty (60 sec.) second decontamination process. The controller 16 can then initialize an internal timer to sixty (60 sec.) seconds so the controller 16 can terminate the decontamination process sixty (60 sec.) seconds after the decontamination process began. Likewise, if the controller 16 determines that the source 12 is separated from the tray table 5 by a distance greater than eighteen (18 in.) inches, but less than twenty four (24 in.) inches, the range indicator 49 can be illuminated yellow and the controller can initialize the timer for a ninety (90 sec.) second decontamination process.

The embodiments described above utilize one or a plurality of electronic proximity sensors 58 that use a sensed capacitance value, reflected light, reflected sound and the like to determine the distance separating the bulbs 14 from the tray table 5. However, other embodiments of the decontamination apparatus 10 can include a probe 58' that can be used instead of, or optionally in addition to the proximity sensor(s) 58 to establish a separation of a suitable distance between the bulbs 14 and the tray table 5 surface to achieve the desired level of decontamination. The probe 58' can be an elongated finger that is pivotally coupled to the housing 20. As the bulbs 14 supported adjacent to that housing 20 are being positioned relative to the tray table 5, the probe 58' is pivoted relative to the housing 20 to extending toward the tray table 5, in a direction that is approximately perpendicular to a plane in which the bulbs 14 are arranged. Establishing contact between a distal tip 71 of the probe 58' and the tray table 15 establishes a separation between the tray table 5 and the bulbs 14 that is a predetermined distance approximately equal to a length of the probe 58'.

In addition to, or instead of adjusting the duration of the decontamination process based on the proximity of the source 12 relative to the tray table 5, the controller 16 can be adapted to adjust the duration of the decontamination process based, at least in part, on the intensity of the UVC light emitted by the bulbs 14 as detected by the intensity sensor(s) 48. For example, if the source 12 is separated from the tray table 5 by a distance of less than 18 inches, but the intensity of the UVC light from the bulbs 14 has declined to a value of approximately 80% of the intensity of the UVC light originally emitted by the bulbs 14, when new, the controller cause the range indicator 49 to be illuminated yellow and set the duration of the decontamination process to be ninety (90 sec.) seconds.

For embodiments where the controller 16 is located remotely (e.g., not physically connected to or supported by the base or other portion of the decontamination apparatus 10) from the decontamination apparatus 10, the controller can optionally be supported on a wall of the room 1, for example. For such embodiments, the controller 16 can be wirelessly connected to communicate with a transceiver provided in place of the controller 16 on the decontamination apparatus.

The redundant occupant sensing system includes a plurality of sensors that each independently senses a different property indicative of the presence or absence of a room occupant. With reference once again to FIG. 1, the redundant occupant sensing system includes a door sensor 54 that is operatively connected to communicate with the controller 16 via a wireless (e.g., Bluetooth, IEEE 802.1x, other short-range communication protocol, etc. . . . ) communication channel and detects a status of the door 6 as being open and/or closed. The door sensor 54 transmits a signal to be received by the controller 16, which can interpret the signal to determine if the door 6 is open, closed, or has changed from open to closed or closed to open. The signal can be embodied by the transmission of an electric signal over a wireless communication channel, or a hardwired connection between the door sensor 54 and the controller 16, or the interruption or establishment of a signal received by the controller 16.

Figure 4:
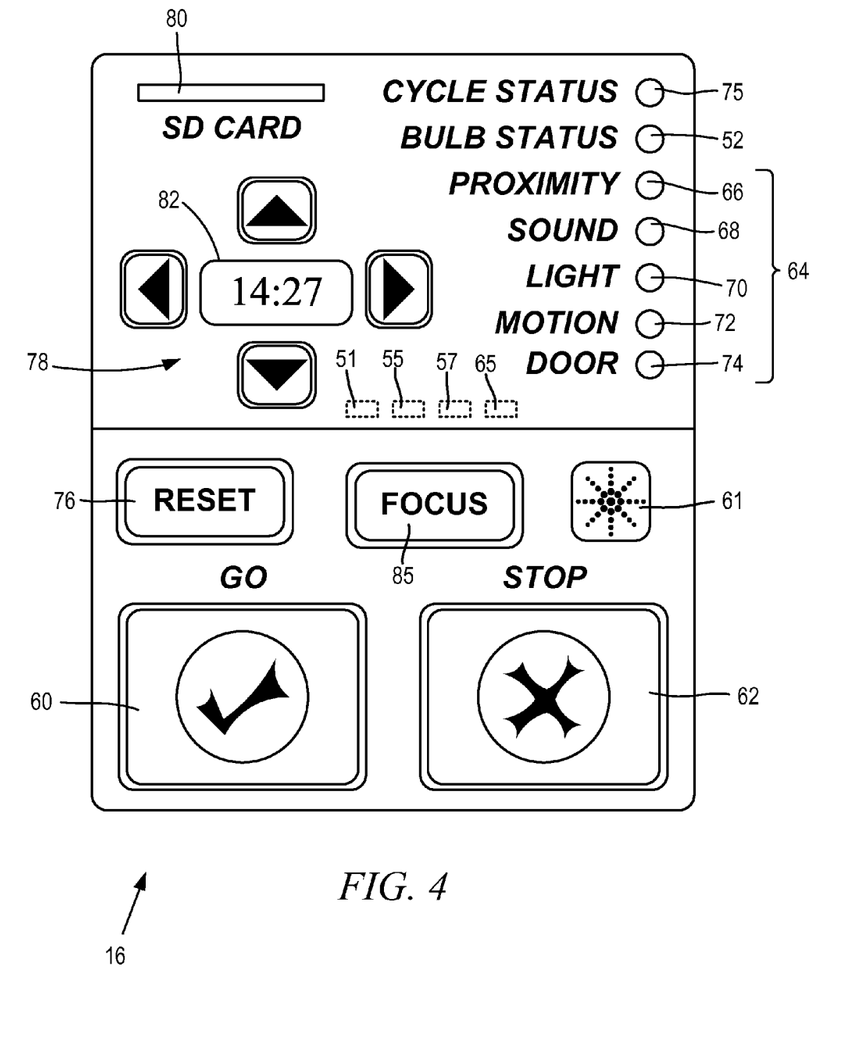
FIG. 4 is a front view schematically depicting a controller of a decontamination system.
Figure 5:
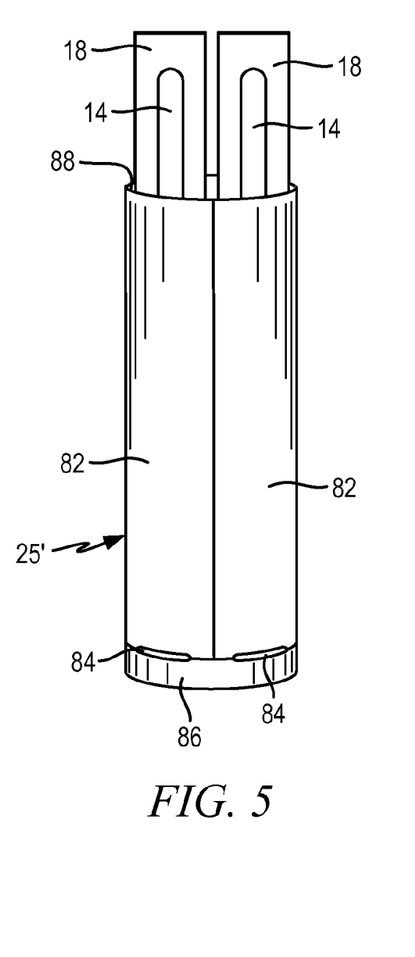
FIG. 5 shows a side view of an alternate embodiment of a decontamination apparatus including a base in a stowed configuration for transportation of the decontamination apparatus.

Other sensors included in the redundant occupant sensing system can likewise be positioned at appropriate locations within the room 1, such as integrated into the controller 16, to detect other properties that would indicate the presence or absence of an occupant. Such other sensors can be discrete sensors, or integrated into a common sensor assembly, which can optionally be housed as part of the controller 16 as shown in FIG. 4 (sensors integrated into the controller 16 in FIG. 4 are represented schematically as broken lines). Regardless of their location and configuration, each of the plurality of sensors in the redundant occupant sensing system must sense a property that the room 1 is unoccupied and communicate this status to the controller 16 before the decontamination process can begin as described below. The unoccupied status, as sensed by the redundant occupant sensing system, must also be maintained while the source(s) 12 of the decontamination apparatus 10 is/are operational, otherwise the controller 16 will terminate operation of operational sources 12.

An example of another of the sensors included in the integrated sensor assembly of the redundant occupant sensing system is an immediate proximity sensor 51 that can detect the presence of an occupant within a predetermined distance from the decontamination apparatus 10 without making physical contact with the occupant. The proximity sensor can utilize any suitable technology such as an electromagnetic field or electromagnetic radiation (infrared, for instance), to determine the distance of an object such as an occupant from the proximity sensor 51 to determine whether the room 1 is occupied. Such a sensor operates by monitoring the electromagnetic field or evaluating the return signal for changes, which would be indicative of the presence of an occupant. Yet other embodiments can utilize an optical sensor that relies on reflected light or the interruption of a beam of light to detect the presence of an occupant, or a capacitive sensor that senses changes in the value of a capacitance sensed within a region of the room 1 where an occupant is likely to be located. Regardless of the sensing mechanism utilized, the proximity sensor signals transmitted to the controller 16 identify changes in the proximity sensor signal that indicate a change has occurred since an earlier proximity sensor signal was transmitted (e.g., when the proximity sensor 51 was normalized under known conditions, such as when the room was unoccupied and the decontamination apparatus 10 was initially powered on).

Another sensor that can optionally be included as part of the integrated sensor assembly is a sound sensor 55. The sound sensor can include a microphone or other sound-sensitive circuit that transmits a signal indicative of the magnitude and/or frequency of sounds audible within the room 1. Similar to the proximity sensor 51 and the other sensors of the redundant occupant sensing system, the sound sensor 55 is operatively connected to communicate with the controller 16 and transmit signals to the controller 16 that are interpretable to indicate changes in the sound level within the bathroom 1. These changes can be relative to the sound level within the room 1 at a time of an earlier sound level is measured, or when the sound sensor 55 is normalized such as when the system is initially powered on when the room is known to be unoccupied.

A light sensor 57 can also optionally be included as part of the sensor assembly to detect changes in light within the room 1. The light sensor 57 can include a photosensitive component such as a photodiode, charge coupled device, etc. . . . , that monitors the intensity of visible light and/or UVC light within the room. Again, a signal indicative of the sensed light levels within the room 1 is transmitted to the controller 16, which can determine whether a change in light level has occurred, which would suggest an occupant has entered the room 1. Contrarily, the light sensor 57 can also sense dramatic reductions in the light within the room 1, and optionally such reductions throughout the entirety of the room 1 (e.g., by utilizing a plurality of light sensors 57 facing different directions). The controller 16 can be initialized and configured to initiate the decontamination process under such circumstances, based on the assumption that the ambient lighting in the room 1 has been turned off when the last occupant has left as described below.

Further, a motion sensor 65 can also optionally be included in the sensor assembly to sense movement within the room 1. Such motion sensors 65 can be sense a property such as changes in the thermal signature at various locations within the room 1. Utilizing the temperature gradients to detect motion is advantageous in that inanimate movement in the room (e.g., a towel falling from a rack) will not trigger the motion sensor 65 to transmit a signal indicative of movement. Other embodiments of the motion sensor 65 include a photoelectric sensor that utilizes a beam of light or and laser that travels from a source to a detector. When an occupant crosses the path of light, the light is blocked and the sensor detects the obstruction. Such motion sensors 65 can optionally be positioned at particularly revealing locations such as approximately 1-3 ft. above the floor at the door 6, for example. Projecting a beam of light at such a location will almost certainly be broken if an occupant enters the room 1 through the door 6.

Certain embodiments of the decontamination system 10 will include at least one of the aforementioned sensors (door, proximity, sound, light and movement), and optionally a plurality, or all of these sensors. However, alternate embodiments can utilize any other suitable sensor(s) that can transmit a signal indicative of the presence of a living occupant within the room 1 without departing from the scope of the present disclosure. For example, a carbon dioxide sensor can be utilized to sense a change in the carbon dioxide level in the room 1 cause by an occupant exhaling. Other embodiments can utilize a heartbeat monitor that can remotely sense the pulses of a beating heart without making physical contact with an occupant. Yet other embodiments can utilize a pressure sensor operatively connected to the bed 4 to sense when an occupant is resting thereon, for example.

An illustrative embodiment of the controller 16 is shown in FIG. 4. As shown, the controller 16 includes a focus button 85 that, when pushed, temporarily energizes or otherwise activates the focal indicator 40 to illuminate that portion of the tray table 5 that is to be decontaminated. Also included are manual override buttons 60, 62 that, when pressed, cause the decontamination process to be manually initiated and stopped on demand, respectively. If the start button 60 is selected, the controller 16 implements a delay of a predetermined duration (e.g., 10 seconds) that is sufficient to allow the person who pressed the start button 60 to exit the room 1 before the UVC bulbs 14 are illuminated as part of the decontamination process. An audible warning such as a repeating beep can be broadcast by a speaker 61 provided to the controller 16 to warn of the impending start of the decontamination process. As mentioned above, the start button 19 on the fob 17 can optionally be selected once the operator has exited the room 1 instead, thereby remotely activating the decontamination cycle.

According to alternate embodiments, however, the controller 16 can optionally be configured to operate in an occupied mode, in which the one or plurality of sensors of the occupant sensing system are deactivated to allow the sources 12 to remain active in the room 1 while the room 1 is occupied by a person. Under certain circumstances, personnel may where personal protective equipment ("PPE") that shields their person from UVC light emitted by the sources 12. The PPE allows personnel to safely work in the environment of the tray table 5 or other surface being decontaminated while the decontamination apparatus 10 is operational without the risk of being exposed to significant levels of UVC light. In an effort to prevent operation of the decontamination apparatus 10 in the occupied mode, each person wearing PPE within the room 1 while the decontamination apparatus 10 is active can wear or possess a badge that can be wirelessly detected within the room 1 by the decontamination apparatus 10. Movement by personnel equipped with the badge can be ignored by the controller 16 such that the controller 16 will not prematurely terminate the decontamination cycle. If, however, movement is sensed outside of the vicinity of such a badge (e.g., movement occurs in a region of the room 1 where a badge is not also present or at least nearby), the controller 16 can determine that an unprotected occupant has entered the room and terminate the decontamination cycle. Thus, in use, personnel can optionally wear the PPE and activate the decontamination apparatus 10 in the occupied mode while continuing to safely work within the room 1 in which the decontamination apparatus 10 is located. Alternately, the decontamination apparatus 10 can be activated in a standard mode, either locally with a delay or remotely from outside of the room 1, and the decontamination apparatus 10 can remain active unless the controller 16 senses the presence of an occupant.

Following the expiration of the delay, each of the sensors included in the redundant occupant sensing system is normalized, indicating a state where it is assumed that the room 1 is unoccupied. If, at any time during the decontamination process any of the sensors senses a property that is indicative of a change from the state in which the sensors were normalized, the controller 16 determines that the room has become occupied, and immediately terminates the decontamination process. To identify the cause of termination, one or a plurality of labeled visible indicators 64 such as discrete LEDs, a liquid crystal display ("LCD"), or any other suitable notification device provided to the controller 16 can be activated. For example, the proximity indicator 66 can be illuminated to indicate that the proximity sensor triggered termination; the sound indicator 68 can be illuminated to indicate that the sound sensor triggered termination; the light indicator 70 can be illuminated to indicate that the light sensor triggered termination; the motion indicator 72 can be illuminated to indicate that the motion sensor triggered termination; and the door indicator 74 can be illuminated to indicate that the door sensor 54 triggered termination. The specific visible indicators 64 included as part of the controller 16 can correspond to the specific sensors present.

Rather than being activated remotely utilizing the fob 17 or locally with the delay, the decontamination apparatus 10 (specifically, the controller 16) can optionally be configured to initiate a decontamination process in response to sensing a change in the sensed light levels in its ambient environment according to alternate embodiments. For example, the controller 16 can optionally be initialized through pressing the start button 19 on the fob 17 three times in quick succession. In response to receiving such a communication from the fob 17, the controller 16 can enter a standby mode and sense the current light level in the room 1. In response to sensing a dramatic drop in the light level relative to the originally-sensed light level, the controller 16 can optionally sound an audible alarm during the delay before subsequently energizing the bulbs 14.

Regardless of the operational mode of the decontamination apparatus 10, if premature termination of the decontamination process occurs before the decontamination process is complete (e.g., before the UVC bulbs 14 have been illuminated for the time required to achieve the desired level of pathogen reduction), a cycle status indicator 75 can be illuminated in a manner indicative of such termination. For example, the cycle status indicator 75 can be illuminated red, and/or made to flash to call an operator's attention to the premature termination of the decontamination process. The manual pressing of a reset button 76 can be required by the controller 16 before the decontamination process can be restarted. Requiring the reset button 76 to be pushed will allow an operator to ensure that the condition resulting in termination of the decontamination apparatus has been cleared before resetting the controller 16. According to alternate embodiments, the cycle status indicator 75 can optionally be provided to the housing 20 of each source 12 as shown in FIG. 2. If a decontamination process is interrupted, each specific source 12 that was interrupted and did not successfully complete the decontamination process can be identified through the state of the cycle status indicator 75 thereon.

Premature termination of the decontamination apparatus can be saved in a log stored on a computer-readable medium (e.g., SD card inserted into SD card port 80 provided to the controller 16, built in hard drive or other non-transitory computer-readable medium provided to the controller 16, remote hard drive or other non-transitory medium remotely located over a hospital communication network) in communication with the controller 16. Such a log can maintain data concerning the cause of an interruption, a time of an interruption, information indicative of the specific room in which premature termination of the decontamination process occurred, and any other data pertaining to the decontaminated state of the room 1. Such data can be utilized to diagnose problems such as a faulty sensor included in the redundant occupant sensing system, and to promote regular decontamination of the room 1.

The controller 16 can optionally be configured to restart a prematurely-terminated decontamination cycle without manual user intervention. For example, once all of the conditions sensed by the sensors in the redundant occupant sensing system return to their normalized values, the controller 16 can initiate a timer to establish a restart delay. If all of the conditions remain at their normalized values for the duration of the restart delay, the controller 16 can automatically restart the decontamination process by once again activating the UVC bulbs 14 for the predetermined cycle time. This process of restarting the decontamination process can optionally be repeated until the decontamination process has been completed successfully. If an automatically restarted decontamination process is successfully completed, the cycle status indicator 75 can reflect the successful completion of the decontamination process.

In the absence of any conditions interrupting the decontamination process, the decontamination process will remain active, with the UVC bulbs 14 illuminated and the redundant occupant sensing system monitoring conditions within the room 1 for any changes that would indicate the entrance of an occupant for a predetermined cycle time. The predetermined cycle time can be manually input and programmed into the controller 16 via a timer input system 78 provided to the controller 16, or can be established through an administration terminal and delivered to the controller 16 via a portable computer-readable medium such as an SD card inserted into an SD card slot 80 provided to the controller 16.

According to alternate embodiments, actions such as adjusting the duration of the decontamination process and actions other than manually initiating the decontamination process can be carried out over a communication network from a remotely-located administration terminal. The cycle time can be independently established to a custom duration for each object to be decontaminated depending on factors such as the size of the room, the number and intensity of the UVC bulbs 14 to be utilized, the distance separating the source 12 from the surface being decontaminated, etc. . . . to achieve the level of decontamination desired to be achieved. For instance, According to alternate embodiments, a default value that can be used for most installations can be utilized. The default value can be selected to be "overkill", meaning that the default duration will be longer than required to achieve the desired level of decontamination for most installations based, at least in part, on assumptions about the size of the room, the number and intensity of the UVC bulbs 14 to be utilized, the distance separating the source 12 from the surfaces to be decontaminated, etc. . . . .

Once the decontamination process has been successfully completed, the cycle status indicator 75 can be illuminated as a solid (i.e., non-flashing) green color or otherwise notify an observer that the decontamination process has been successfully completed. Additionally, successful completion of the decontamination process can be logged on the computer-readable medium in communication with the controller 16, documenting a time when the room was last successfully decontaminated.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:
1. A decontamination apparatus comprising:
   a base;
   a source that emits UVC light at a suitable intensity to at least partially decontaminate a target object on which the UVC light is imparted to render the target object pathogen reduced;

an adjustable support coupled to the base that supports the source, the adjustable support comprising an adjustment mechanism that is manipulable to adjust a position of the source relative to the base;

a range sensor that senses a property indicative of a distance separating the source of UVC light from the target object to be rendered pathogen reduced;

a range indicator operatively connected to the range sensor to receive a signal indicative of the distance separating the source from the target object and issue a notification that the source is positioned within a suitable distance from the target object to achieve a desired level of pathogen reduction within an exposure time having a predetermined length established before activation of the source; and a controller operatively connected to the source to control emission of the UVC light and maintain emission of the UVC light for at least the exposure time having the predetermined length once the source is activated.

2. The decontamination apparatus according to claim 1, wherein the adjustable support comprises an articulated arm coupled adjacent to a proximate end to the base and coupled adjacent to a distal end to the source.

3. The decontamination apparatus according to claim 1, wherein the range sensor comprises a receiver that receives at least one of reflected light and sound as the property indicative of the distance separating the source of UVC light from the target object.

4. The decontamination apparatus according to claim 1 further comprising a range indicator that issues an alert to notify an operator of a condition pertaining to the distance separating the source from the target object.

5. The decontamination apparatus according to claim 1, wherein the source comprises:

a UVC bulb that is operable to emit the UVC light; and
a reflective shield arranged adjacent to the UVC bulb to reflect at least a portion of the UVC light emitted by the UVC bulb generally away from the target object, in a focused direction generally toward the target object.

6. The decontamination apparatus according to claim 1 further comprising a plurality of proximity sensors that each detect a different property indicative of an occupant's presence within a predetermined proximity to the decontamination apparatus where the occupant will be exposed to UVC light emitted by the source.

7. The decontamination apparatus according to claim 1 further comprising a battery provided to the base to supply electric energy for energizing the source and operating the control section.

8. The decontamination apparatus according to claim 1 further comprising at least one additional source that emits UVC light at a suitable intensity to at least partially decontaminate the target object and render the target object pathogen reduced, wherein the source and the additional source are each coupled to a distal end of a different articulated arm as the adjustable support.

9. The decontamination apparatus according to claim 2, wherein the articulated arm comprises a hinge arranged along the arm between the base and the source, the hinge being adjustable to pivotally adjust the position of the source to position the source within a predetermined proximity to the target object to achieve a desired level of decontamination during a decontamination process with a predetermined duration.

10. The decontamination apparatus according to claim 4, wherein the condition comprises the source being separated further from the target object than a maximum distance beyond which a desired level of pathogen reduction of the target object will not be achieved during the decontamination process.

11. The decontamination apparatus according to claim 4, wherein the condition comprises the source being separated closer to the target object than a maximum distance beyond which a desired level of pathogen reduction of the target object will not be achieved during the decontamination process.

12. The decontamination apparatus according to claim 5, wherein the reflective shield comprises a plurality of arcuate regions, each with a different radius of curvature.

13. The decontamination apparatus according to claim 6, wherein the control section is operatively connected to the plurality of proximity sensors to receive signals indicative of the occupant's presence within the predetermined proximity and interrupt emission of the UVC light from the source.

14. The decontamination apparatus according to claim 6, wherein the plurality of proximity sensors comprises all of:

an immediate proximity sensor that senses movements of the occupant occurring within the predetermined distance from the decontamination apparatus, a sound sensor that senses audible sounds resulting from the occupant's presence within the predetermined distance from the decontamination apparatus, and a light sensor that senses changes in light resulting from the occupant's presence within the predetermined distance from the decontamination apparatus.

15. The decontamination apparatus according to claim 8, wherein each of the different articulated arms comprises a first segment that is telescopically adjustable relative to a second segment to adjust a length of the articulated arm.

16. A decontamination apparatus comprising:

a base;

a first arm adjustably coupled to the base to allow an orientation of the first arm to be adjusted relative to the base, the first arm comprising an adjustable segment that allows a length of the arm to be adjusted;

a first source coupled adjacent to a distal end of the arm, wherein the first source emits UVC light at a suitable intensity to at least partially decontaminate a first target object on which the UVC light is imparted to render the first target object pathogen reduced;

a controller operatively connected to the first source to control emission of the UVC light onto the first target object;

a second arm adjustably coupled to the base to allow an orientation of the second arm to be adjusted relative to the base, the second arm comprising an adjustable segment that allows a length of the second arm to be adjusted; and a second source coupled adjacent to a distal end of the second arm and operatively connected to be controlled by the controller, wherein the second source emits UVC light at a suitable intensity to at least partially decontaminate a second target object on which the UVC light from the second source is imparted to render the second target object pathogen reduced.

17. The decontamination apparatus according to claim 16, wherein the first arm comprises at least one of a plastically deformable region that is manually bendable to establish a desired position of the source relative to the target object, and a hinge that allows a portion of the first arm to be pivotally adjusted relative to at least one of the base and another portion of the first arm.

18. The decontamination apparatus according to claim 16, wherein the controller controls operation of the first source independently of the second source.

19. The decontamination apparatus according to claim 16 further comprising a battery provided to the base to supply electric energy for energizing the first and second sources and operating the controller.

20. The decontamination apparatus according to claim 16 further comprising:
   a range sensor provided to each of the first source and the second source, the range sensors being operable to sense a property indicative of a distance separating the target object from its respective source, wherein
      the controller controls emission of the UVC light from the first and second sources in response to receiving a signal indicative of the distance sensed by the respective range sensors and comprises a variable component that establishes at least one of a duration of a decontamination process and the suitable intensity of UVC light independently for each of the first and second sources.

21. The decontamination apparatus according to claim 16, wherein the first arm comprises a hinge arranged along the arm between the base and the source, the hinge being adjustable to pivotally adjust the position of the source relative to the base to position the source within a predetermined proximity to the target object suitable to achieve a desired level of decontamination during a decontamination process with a predetermined duration.

22. The decontamination apparatus according to claim 18 further comprising a plurality of proximity sensors that each detect a different property indicative of an occupant's presence within a predetermined proximity to the decontamination apparatus where the occupant will be exposed to UVC light emitted by the source, wherein the controller interferes with operation of the first source and the second source in response to a determination that the occupant is present within the predetermined proximity based on a signal from at least one of the plurality of proximity sensors.

* * * * *